United States Patent
Umeno

(10) Patent No.: US 6,428,774 B1
(45) Date of Patent: Aug. 6, 2002

(54) NONAQUEOUS LIQUID COSMETIC

(75) Inventor: Takashi Umeno, Gunma (JP)

(73) Assignee: Mitsubishi Pencil Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/597,052

(22) Filed: Jun. 20, 2000

(30) Foreign Application Priority Data

Jul. 6, 1999 (JP) .............................. 11-192121

(51) Int. Cl.$^7$ .......................... A61K 7/021; A61K 7/00
(52) U.S. Cl. ......................................... 424/63; 424/401
(58) Field of Search ................... 424/401, 63

(56) References Cited

U.S. PATENT DOCUMENTS 6,121,373 A * 9/2000 Starch ..................... 524/837
6,139,823 A * 10/2000 Dreschsler et al. ........... 424/64

* cited by examiner

*Primary Examiner*—Jose' G. Dees
*Assistant Examiner*—Konata M. George
(74) *Attorney, Agent, or Firm*—Darby & Darby

(57) ABSTRACT

A liquid cosmetic comprising a non-water soluble principal solvent A, a water soluble auxiliary solvent B, a preservative C and a coloring component D as essential components, wherein the principal solvent A is not substantially miscible with the auxiliary solvent B, and the auxiliary solvent B is dispersed in the principal solvent A; and most of the preservative C is distributed into the dispersed auxiliary solvent B. The principal solvent A is preferably selected from octamethylcyclotetrasiloxane and decamethylcyclopentasiloxane; the auxiliary solvent B is preferably selected from propylene glycol, 1,3-butylene glycol and dipropylene glycol; and the preservative C is preferably selected from Parabens.

Provided is the nonaqueous liquid cosmetic which inhibits putrefaction by microorganisms even if droplets of sweat and saliva are introduced into the cosmetic and which is free of bittersweet felt unpleasant by a user.

16 Claims, No Drawings

NONAQUEOUS LIQUID COSMETIC

BACKGROUND OF THE INVENTION

1. Field of the Invention

The present invention relates to a nonaqueous liquid cosmetic, specifically to a nonaqueous hydrophobic liquid make-up cosmetic having a viscosity of 100,000 mPa·s or less at 25° C., usually called a liquid cosmetic, wherein sundry bacteria are inhibited from propagating when an aqueous contaminant such as sweat and saliva is involved.

2. Description of the Related Art

In using a make-up liquid cosmetic such as liquid rouge and liquid eye shadow filled in a container for a liquid coating cosmetic equipped with an applicator of a brush or sponge type, sweat and saliva stick to fibers of a brush part in the applicator in a certain case. Usually, a preservative and a fungicide are contained in these liquid cosmetics to inhibit sundry bacteria mixed therein from propagating. However, if this liquid cosmetic is a nonaqueous hydrophobic liquid cosmetic, droplets of sweat and saliva mixed therein are not miscible with the liquid content and are involved as they are in liquid vehicles in a certain case.

The involved droplets cause putrefaction by microorganisms as time passes, and as a result, such a problem that a putrefactive odor is generated from the tip of a brush has been brought about in many cases. If a liquid cosmetic is a nonaqueous hydrophobic cosmetic, Parabens are effective as a substantially usable preservative from the viewpoints of safety to a human body, irritation to the skin and the mucosa and easiness (stability in a dispersion system) in blending with the vehicle. However, Parabens are lipophilic, and therefore when it is blended with a nonaqueous hydrophobic cosmetic, it is dissolved into the vehicle, so that it is not distributed into droplets comprising water as a main component which is secondarily involved later. Accordingly, a preservative system comprising primarily only Parabens has not been able to prevent a foul odor at a brush part caused by the droplets which was involved during use and degenerated with the passage of time.

A cosmetic filled in a container for a liquid coating cosmetic equipped with an applicator of a brush or sponge type has to be liquid, and the liquid is liable to introduce droplets of sweat and saliva. Further, the water introduced thereinto is not evaporated and is liable to bring about putrefaction by microorganisms.

An object of the present invention is to provide a nonaqueous hydrophobic liquid make-up cosmetic having a viscosity of 100,000 mPa·s at 25° C., usually called a liquid cosmetic, wherein the cosmetic inhibits putrefaction by microorganisms even if droplets of sweat and saliva are introduced and is free of a bittersweet taste felt unpleasant by a user. Further, an object of the present invention is to provide a nonaqueous hydrophobic liquid make-up cosmetic which can maintain a stable dispersing state without causing separation of the cosmetic after storage over a long period of time, particularly even in a dispersion system using an inorganic pigment having a large specific gravity.

SUMMARY OF THE INVENTION

Various investigations continued by the present inventors in order to achieve the subjects described above have resulted in finding that microbial putrefaction can be inhibited to a large extent by using two kinds of solvents in a liquid cosmetic and distributing (dissolving) most of a preservative in a water-soluble solvent so that the preservative is dispersed homogeneously in a principal non-water soluble solvent, and thus the present invention has been completed.

That is, the present invention relates to a nonaqueous liquid cosmetic comprising a non-water soluble principal solvent A, a water soluble auxiliary solvent B, a preservative C and a coloring component D as essential components, wherein the principal solvent A is not substantially miscible with the auxiliary solvent B, and the auxiliary solvent B is dispersed in the principal solvent A; and the preservative C is distributed (dissolved) in the dispersed auxiliary solvent B.

In the invention described above, the distribution factors (solubility) of the preservative C into the principal solvent. A and the auxiliary solvent B reside preferably in a relation of $A \leq B$ in order to distribute the preservative C to the auxiliary solvent B.

In the present invention, it is preferred in terms of the efficacy of preventing putrefaction and a foul odor caused by secondary contamination and a stability with the passage of time that a blending ratio of the auxiliary solvent B/the preservative C is 1.5 to 35 in terms of a weight ratio and that a blending amount of the auxiliary solvent B falls in a range of 0.5 to 10 wt % based on the liquid cosmetic.

Further, it is preferred in the invention described above that fine droplets of the solvent B dissolving the preservative C, a coloring component and other make-up components are homogeneously dispersed in the principal solvent A and that water is not substantially contained therein.

According to the present invention, even if droplets of sweat and saliva are introduced into the cosmetic, the water (sweat and saliva) is involved in the water-soluble auxiliary solvent B, which is homogeneously dispersed, and hence the preservative present in the solvent B displays a preservative effect on the water. This inhibits microbial putrefaction caused by the water (sweat and saliva) mixed therein. Further, a stable dispersion system can be maintained even in storage over a long period of time without causing separation of the cosmetic, and in particular, even a dispersion system in which an inorganic pigment having a large specific gravity is used has a high dispersion stability.

DETAILED DESCRIPTION OF THE PREFERRED EMBODIMENTS

The constitution and an embodiment of the present invention shall be explained below in detail.

The present invention relates to a nonaqueous hydrophobic liquid cosmetic having a viscosity of 100,000 mPa·s at 25° C., called a make-up liquid cosmetic such as liquid rouge and liquid eye shadow.

The liquid cosmetic of the present invention may be blended so that it contains various components, however it contains a non-water soluble principal solvent A, a water soluble auxiliary solvent B, a preservative C and a coloring component D as the essential components, which shall be explained below.

First of all, the principal solvent A is a non-water soluble solvent which does not substantially exert an adverse effect on a human body and is selected from silicone oils which have so far been used for cosmetics. For example, diorganopolysiloxanes and cyclic siloxanes having a viscosity of a low viscosity extending to a high viscosity can be used. In particular, most preferred is at least one selected from octamethylcyclotetrasiloxane, decamethylcyclopentasiloxane, tetramethyltetraphenylcyclotetrasiloxane and the like, which are the cyclic siloxanes. This principal solvent A is used in a range of 5 to 80 wt %, preferably 10 to 50 wt % in the liquid cosmetic.

Next, the auxiliary solvent B is selected from polyhydric alcohol base compounds which are basically water-soluble and are not miscible (mutually dissolved) with the principal solvent A described above and which do not exert an adverse effect on a human body.

It is preferably at least one glycol selected from, for example, propylene glycol, 1,3-butylene glycol, dipropylene glycol and the like.

This auxiliary solvent B is used in a range of 11 wt % or less, preferably 0.5 to 10 wt % and more preferably 2 to 10 wt % in the liquid cosmetic. If it is too small, practical effects such as prevention of putrefaction and a foul odor are reduced, and if it is too large, it is not preferred in terms of taste evaluation and stability with the passage of time. A blending ratio of the principal solvent A/the auxiliary solvent B falls preferably in a range of 3 to 20 in terms of a weight ratio.

Paraben which has so far been used for cosmetics is preferred as the preservative C.

Preferred is at least one selected from, for example, methyl para-hydroxybenzoate, ethyl para-hydroxybenzoate, propyl para-hydroxybenzoate, butyl para-hydroxybenzoate and isopropyl para-hydroxybenzoate. The preservative C is particularly preferably selected so that the selected preservative C has distribution factors to the principal solvent A and the auxiliary solvent B to be in a relation of A≦B.

In this case, the distribution factors are defined by the solubilities of the preservative C in the principal solvent A and the auxiliary solvent B under a condition of 25° C. This preservative C is used in a range eof 0.15 to 0.8 wt %, preferably 0.2 to 0.6 wt % in the liquid cosmetic. If it is too smaller than this range, practical effects such as prevention of putrefaction and a foul odor are reduced, and if it is too larger than this range, it is not preferred in terms of taste evaluation, irritation to the skin and stability with the passage of time.

A blending ratio of the auxiliary solvent B/the preservative C falls preferably in a range of 1.5 to 35, preferably 5 to 30 in terms of a weight ratio.

Inorganic and organic pigments, dyes, lakes and, if necessary, other colorants are used as the coloring component D. It includes, for example, inorganic pigments-such as carmine, iron oxide, mica and titanium dioxide, extender pigments such as a tar pigment and a lake thereof and talc, carbon black, chromium oxide, chromium hydroxide, cochineal, a red koji pigment, ultramarine blue and manganese violet. This coloring component D is used in a range of 1 to 50 wt %, preferably 5 to 30 wt % in the liquid cosmetic.

A dispersion state of the solvent B in the solvent A shall not specifically be restricted, and various states such as, for example, colloid, micell, liquid crystal, emulsion and suspension can be considered. It is suitably settled according to the characteristics of the desired cosmetic and the properties of the solvents and the other additives. The preservative C may be in a state that most of it is dispersed or dissolved in the solvent B to be distributed therein or may be in a state that it is adsorbed on a solid content such as a pigment as the coloring component D and other resin components added to the cosmetic. A part of the preservative C staying in the composition described above may form a complex with a resin component (a thickening resin, a fixing resin and the like).

The particularly preferred embodiment of the present invention is that the fine droplets of the solvent B dissolving the preservative C., the coloring component and the other make-up components are homogeneously dispersed in the principal solvent A and that water is not substantially contained therein. In this case, the fine droplets of the solvent B are homogeneously dispersed in the vehicles of the principal solvent A which is not substantially miscible with the auxiliary solvent B in a state that a prescribed amount of the preservative C (Paraben) is dissolved in the auxiliary solvent B (glycol) of 5 to 30 times the amount of the preservative C. In order to prevent the droplets of the solvent B dissolving the preservative C finely dispersed in the vehicles from being ejected out of the vehicles by a change with the passage of time, it is particularly preferable to add a thickener and a fixing resin as the other cosmetic components and oil & fat, wax and the like for providing an effect of improving a touch to the skin to stabilize the system.

The thickener used in this case is at least one selected from bentonite, organic bentonite, silicic acid anhydride, silica, sodium magnesium silicate, aluminum magnesium silicate, hectorite, montmorillonite, and cationic surfactant-treated materials or organic covered materials thereof.

This thickener is used in a range eof 0.5 to 10 wt %, preferably 1.5 to 5 wt % in the liquid cosmetic.

Further, trimethylsiloxy silicate having a chemical formula: $[(CH_3)_3SiO_{1/2}]_x \cdot [SiO_2]_y$,(wherein x=1 to 3, and y =0.5 to 8) is preferably blended. In this case, the preferred effect is displayed in a coating cosmetic of a brush or sponge type such as liquid rouge and liquid eye shadow in which an inorganic pigment such as titanium oxide and mica used as a coloring component is fixed on the skin or labial mucosa by a resin film of the above trimethylsiloxy silicate to develop a color.

An oil component such as oil & fat and wax is used for the effects of improving a touch to the skin in using the cosmetic and for a function as a plasticizer for the fixing resin. The oil component used for such objects includes diusostearyl malate, liquid paraffin, isopropyl palmitate, 2-ethylhexanoic acid triglyceride, beef tallow, isostearic acid, hydrogenated oil, vaseline, lanolin, sorbitan monooleate, cetanol, Japan wax, earth wax, carnauba wax and solid paraffin.

In addition thereto, propylene carbonate and methylphenylpolysiloxane can suitably be added, if necessary, as a gelation auxiliary used for thickening a cosmetic liquid.

When Paraben is used as the preservative C in the nonaqueous hydrophobic liquid make-up cosmetic of the present invention, though not specifically be restricted, the solubilities of Paraben in the solvents A and B satisfy preferably the following relation:

water (saliva, sweat and the like)<<principal solvent A (octamethylcyclotetrasiloxane, decamethylcyclopentasiloxane and the like)<<auxiliary solvent B (propylene glycol, 1,3-butylene glycol, dipropylene glycol and the like).

Thus, Paraben, which is the preservative C is distributed more into the droplets of the auxiliary solvent B (glycols), and once water (saliva, sweat and the like) is introduced into the cosmetic liquid, more Paraben than such the amount that microorganisms can be prevented from growing is dissolved into the introduced water. Glycols have a high solubility in water, and therefore if water is mixed in the system, glycols coming into contact with the water mixed therein move into the water. This moving of glycols is accompanied with moving of Paraben into the water phase to display a preservative effect.

The nonaqueous liquid cosmetic of the present invention can readily be produced by homogeneously mixing prescribed amounts of the respective components which are prepared in advance in an optional order by means of a turbine mixer or a stirred mixing tank which has so far been publicly known. In this case, particularly when the distribution factors of the preservative C into the principal solvent A and the auxiliary solvent B are almost the same, it is preferred that the preservative C is homogeneously dissolved or dispersed in advance in the auxiliary solvent B and then homogeneously dispersed in the principal solvent A together with or separately from the other cosmetic components such as the colorant. On the other hand, when the distribution factors of the preservative C into the principal solvent A and the auxiliary solvent B reside in a relation of A<<B, the preservative C and the auxiliary solvent B may be mixed into the principal solvent A at the same time to be homogeneously dispersed. In this case, the preservative C is selectively distributed into the auxiliary solvent B.

EXAMPLES

The present invention shall be explained below in further details with reference to examples and comparative examples, but the present invention shall not be restricted by these examples.

Evaluation test methods used for the examples shall be shown below.

(1) Preservative Efficacy Test

Test bacterial strain: bacteria group {*Escherichia coli* ATCC8739, *Pseudomonas aeruginosa* ATCC9027, *Staphylococcus aureus* ATCC6538} fungi group {*Candida albicans* ATCC10231, *Aspergillus niger* ATCC16404}

Test method

The test strains were pre-cultured for 24 hours (until generation of spores in the case of *Aspergillus niger*) and suspended respectively in a 0.5% Tween 80 physiological salt solution. The bacteria or fungi amounts were controlled so as to be $10^8$/ml, respectively. One tenth ml of each solution thus prepared for bacteria or fungi group were inoculated on 20 g of each test specimen provided for the bacteria group and the fungi group.

Sampled was 0.1 ml from the specimens inoculated after 2 hours, 24 hours, 48 hours, 72 hours, 7 days and 14 days since the inoculation, and smeared were the bacteria group on an SCDLP agar plate culture medium and the fungi group on a GPLP agar plate culture medium, and they were cultured at 30° C. for 24 to 72 hours to determine the survived bacteria and fungi amounts. The inoculated specimens were stored under a constant temperature atmosphere of 25° C.

<Judgement>
- ◎: The bacteria group or fungi group were extinct or decreased less than 10 pieces/ml in a detectable bacteria or fungi amount in 3 days or shorter after inoculation
- ○: ditto in 7 days or shorter after inoculation
- Δ: ditto in 14 days or shorter after inoculation
- X: bacteria or fungi were found for 14 days or longer after inoculation (2) Practical (microorganism) Test ① The specimen filled into a cosmetic container of a brush type is sufficiently discharged to the brush part by an ordinary liquid-discharging operation. This is subjected to brush conditioning on a wood free paper to sufficiently spread the liquid content into the brush part. This is repeated 10 times.

② *Pseudomonas aeruginosa* ATCC9027 and *Staphylococcus aureus* ATCC6538 are suspended in an SCD liquid culture medium diluted to 200 times so that the bacteria amounts become $10^5$/ml respectively. This suspension is filled in a Petri dish so as to be 1 mm in depth.

③ Only the brush part of the cosmetic in ① is sufficiently immersed in this Petri dish and rubbed against the bottom of the dish so that the bacterial suspension penetrates into the fibers of the brush.

④ A cap is installed to this body, and the cosmetic is stored under an environment of a temperature of 30° C. and a humidity of 90% RH.

⑤ The brush part of the stored specimen is rubbed on the SCD liquid culture medium in the shape of a check after 24 hours, 48 hours, 72 hours, 7 days and 14 days to culture the bacteria on this plate culture medium at 32° C. for 48 hours.

⑥ Judgement is made with a storage time elapsed until microorganisms are not found and showed by the following criteria:
- ◎: microorganisms became undetected within 2 days
- ○: microorganisms became undetected within 3 days
- Δ: microorganisms became undetected within 7 days
- X: microorganisms still remain for 7 days or more (3) Taste Evaluation Unpleasant bittersweet felt when the specimen liquid came into a mouth was sensibly evaluated by an expert panel.

<Judgement>
- ◎: Unpleasant taste is not felt
- X: Unpleasant bittersweet taste is felt (4), Stability with the Passage of Time The specimen liquid is filled into a cosmetic container of a brush type. A cap is installed thereto, and the container is stored in an unused state in a 40° C. constant temperature atmosphere with the brush turned up.

Evaluation is visually made by observing the specimen liquid discharged from the brush part with an ordinary discharging operation after storing for a fixed period of time. The specimen from which liquid is discharged normally is regarded as acceptance and evaluation is made evaluation is made by a period of time during which a transparent liquid is notably observed.

<Judgement>
- ◎: Normal for 2 months or longer
- ○: Normal for one month or longer
- Δ: Normal for 2 weeks or shorter
- X: Separated immediately after produced Examples 1 to 6 and Comparative Examples 1 to 4

A nonaquerus principal solvent A, a water-soluble auxiliary solvent B, a preservative C and a coloring component D as the essential components and the other cosmetic components were blended as shown in Tables 1 and 2, and the blending amounts were altered so that specimens of liquid cosmetics having the respective blending compositions as shown in Tables 1 and 2 were prepared by means of a Talton universal mixing stirrer (5DMV-01-rr type). Paraben of the preservative C used had a higher solubility in 1,3-butylene glycol of the auxiliary solvent B than in the principal solvent A used, and the specimens were produced by a method in which Paraben was dissolve d in advance in the auxiliary solvent B and then dispersed in the principal solvent A . The respective specimens thus obtained were used to carry out the various evaluation tests described above. The evaluation results of the tests are shown together in Tables 1 and 2.

In Comparative Example 2, the system was unstable and separated during storage, so that the practical tests could not be carried out.

The bittersweet taste felt in Example 1 originates in 1,3-butylene glycol.

TABLE 1

|   | Components | Example 1 | 2 | 3 | 4 |
|---|---|---|---|---|---|
| A | Octamethylcyclotetrasiloxane | 20 | 20 | 20 | 20 |
| A | Decamethylcyclopentasiloxane | 10 | 10 | 10 | 10 |
| D | Micaceous titanium | 10 | 10 | 10 | 10 |
| D | Legal pigment Red No. 202 | 3 | 3 | 3 | 3 |
|   | Trimethylsiloxy silicate | 15 | 15 | 15 | 15 |
|   | Organic bentonite | 3.5 | 3.5 | 3.5 | 3.5 |
|   | Propylene carbonate | 0.5 | 0.5 | 0.5 | 0.5 |
|   | Diisostearyl malate | 23.6 | 23.6 | 23.6 | 23.6 |
|   | Liquid paraffin | 10 | 12 | 4 | 5.1 |
| C | Methyl para-hydroxybenzoate | 0.1 | 0.1 | 0.1 | 0.1 |
| C | Ethyl para-hydroxybenzoate | 0.1 | 0.1 | 0.1 | 0.05 |
| C | Propyl para-hydroxybenzoate | 0.1 | 0.1 | 0.1 | 0.05 |
| C | Butyl para-hydroxybenzoate | 0.1 | 0.1 | 0.1 | 0.1 |
| B | 1,3-Butylene glycol | 4 | 2 | 10 | 9 |
|   |   | 100 | 100 | 100 | 100 |
| Evaluation | Preservative test | ⊚ | ⊚ | ⊚ | ⊚ |
|   | Practical test | ⊚ | ⊚ | ⊚ | ⊚ |
|   | Taste evaluation | ⊚ | ⊚ | ⊚ | ⊚ |
|   | Stability with the passage of time | ⊚ | ⊚ | ⊚ | ⊚ |

TABLE 2

|   | Components | Comparative Example 1 | 2 |
|---|---|---|---|
| A | Octamethylcyclotetrasiloxane | 20 | 20 |
| A | Decamethylcyclopentasiloxane | 14 | 10.4 |
| D | Micaceous titanium | 10 | 10 |
| D | Legal pigment Red No. 202 | 3 | 3 |
|   | Trimethylsiloxy silicate | 15 | 15 |
|   | Organic bentonite | 3.5 | 3.5 |
|   | Propylene carbonate | 0.5 | 0.5 |
|   | Diisostearyl malate | 23.6 | 23.6 |
|   | Liquid paraffin | 10 | 10 |
| C | Methyl para-hydroxybenzoate | 0.1 |  |
| C | Ethyl para-hydroxybenzoate | 0.1 |  |
| C | Propyl para-hydroxybenzoate | 0.1 |  |
| C | Butyl para-hydroxybenzoate | 0.1 |  |
| B | 1,3-Butylene glycol |  | 4 |
|   |   | 100 | 100 |
| Evaluation | Preservative test | Δ | X |
|   | Practical test | X | X |
|   | Taste evaluation | ⊚ | ⊚ |
|   | Stability with the passage of time | ⊚ | ⊚ |

What is claimed is:

1. A nonaqueous liquid cosmetic consisting essentially of a non-water soluble principal solvent A selected from the group consisting of diorganopolysiloxanes and cyclic siloxanes, a water soluble auxiliary solvent B selected from glycol compounds, a preservative C and a coloring component D, wherein the principal solvent A is not substantially miscible with the auxiliary solvent B, and the auxiliary solvent B is dispersed in the principal solvent A; and the preservative C is distributed in the dispersed auxiliary solvent B.

2. The nonaqueous liquid cosmetic as described in claim 1, wherein the distribution factors (solubility) of the preservative C into the principal solvent A and the auxiliary solvent B reside in a relation of A≦B.

3. The nonaqueous liquid cosmetic as described in claim 1, wherein fine droplets of the solvent B dissolving the preservative C, the coloring component and other cosmetic components are homogeneously dispersed in the principal solvent A, and water is not substantially contained therein.

4. The nonaqueous liquid cosmetic as described in claim 2, wherein fine droplets of the solvent B dissolving the preservative C, the coloring component and other cosmetic components are homogeneously dispersed in the principal solvent A, and water is not substantially contained therein.

5. The nonaqueous liquid cosmetic as described in claim 3, wherein at least a thickener and oil & fat are blended as the cosmetic components.

6. The nonaqueous liquid cosmetic as described in claim 4, wherein at least a thickener and oil & fat are blended as the cosmetic components.

7. The nonaqueous liquid cosmetic as described in claim 1, wherein a blending ratio of the auxiliary solvent B/the preservative C is 1.5 to 35 in terms of a weight ratio, and a blending amount of the auxiliary solvent B falls in a range of 0.5 to 10% based on the total amount of the nonaqueous liquid cosmetic.

8. The nonaqueous liquid cosmetic as described in claim 2, wherein a blending ratio of the auxiliary solvent B/the preservative C is 1.5 to 35 in terms of a weight ratio, and a blending amount of the auxiliary solvent B falls in a range of 0.5 to 10% based on the total amount of the nonaqueous liquid cosmetic.

9. The nonaqueous liquid cosmetic as described in claim 3, wherein a blending ratio of the auxiliary solvent B/the preservative C is 1.5 to 35 in terms of a weight ratio, and a blending amount of the auxiliary solvent B falls in a range of 0.5 to 10% based on the total amount of the nonaqueous liquid cosmetic.

10. The nonaqueous liquid cosmetic as described in claim 4, wherein a blending ratio of the auxiliary solvent B/the preservative C is 1.5 to 35 in terms of a weight ratio, and a blending amount of the auxiliary solvent B falls in a range of 0.5 to 10% based on the total amount of the nonaqueous liquid cosmetic.

11. The nonaqueous liquid cosmetic as described in claim 1, wherein the principal solvent A is at least one selected from octamethylcyclotetrasiloxane and decamethylcyclopentasiloxane; the auxiliary solvent B is at least one selected from propylene glycol, 1,3-butylene glycol and dipropylene glycol; and the preservative C is at least one selected from Parabens.

12. The nonaqueous liquid cosmetic as described in claim 2, wherein the principal solvent A is at least one selected from octamethylcyclotetrasiloxane and decamethylcyclopentasiloxane; the auxiliary solvent B is at least one selected from propylene glycol, 1,3-butylene glycol and dipropylene glycol; and the preservative C is at least one selected from Parabens.

13. The nonaqueous liquid cosmetic as described in claim 3, wherein the principal solvent A is at least one selected from octamethylcyclotetrasiloxane and decamethylcyclopentasiloxane; the auxiliary solvent B is at least one selected from propylene glycol, 1,3-butylene glycol and dipropylene glycol; and the preservative C is at least one selected from Parabens.

14. The nonaqueous liquid cosmetic as described in claim 4, wherein the principal solvent A is at least one selected from octamethylcyclotetrasiloxane and decamethylcyclopentasiloxane; the auxiliary solvent B is at least one selected from propylene glycol, 1,3-butylene glycol and dipropylene glycol; and the preservative C is at least one selected from Parabens.

15. The nonaqueous liquid cosmetic as described in claim 7, wherein the principal solvent A is at least one selected from octamethylcyclotetrasiloxane and decamethylcyclopentasiloxane; the auxiliary solvent B is at least one selected from propylene glycol, 1,3-butylene glycol and dipropylene glycol; and the preservative C is at least one selected from Parabens.

16. A make-up cosmetic instrument comprising a container for a liquid coating cosmetic equipped with an applicator of a brush or sponge type charged with the nonaqueous liquid cosmetic as described in claim 1.

* * * * *